United States Patent
Bitler et al.

(10) Patent No.: US 7,449,511 B2
(45) Date of Patent: *Nov. 11, 2008

(54) POLYMERIC THICKENERS FOR OIL-CONTAINING COMPOSITIONS

(75) Inventors: Steven P. Bitler, Menlo Park, CA (US); David D. Taft, Atherton, CA (US)

(73) Assignee: Landec Corp., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/199,508

(22) Filed: Aug. 8, 2005

(65) Prior Publication Data

US 2005/0272618 A1  Dec. 8, 2005

Related U.S. Application Data

(60) Division of application No. 09/810,920, filed on Mar. 16, 2001, now Pat. No. 6,989,417, which is a continuation-in-part of application No. 09/398,377, filed on Sep. 17, 1999, now Pat. No. 7,101,928.

(51) Int. Cl.
*C08K 5/101* (2006.01)
(52) U.S. Cl. ...................... 524/474; 524/801
(58) Field of Classification Search ................ 524/474, 524/801; 514/772.4, 772.6
See application file for complete search history.

(56) References Cited

U.S. PATENT DOCUMENTS

| | | | |
|---|---|---|---|
| 3,355,394 A | 11/1967 | Korbanka et al. | |
| 3,772,196 A | 11/1973 | St Clair et al. | |
| 3,892,671 A | 7/1975 | Song et al. | |
| 3,894,958 A | 7/1975 | McCoy et al. | |
| 3,915,843 A | 10/1975 | Franck et al. | |
| 3,915,961 A | 10/1975 | Sellstadt | |
| 4,057,622 A | 11/1977 | Hase et al. | |
| 4,057,623 A | 11/1977 | Hase et al. | |
| 4,057,624 A | 11/1977 | Hase et al. | |
| 4,128,634 A | 12/1978 | Hase et al. | |
| 4,128,635 A | 12/1978 | Hase et al. | |
| 4,128,636 A | 12/1978 | Hase et al. | |
| 4,261,845 A | 4/1981 | Cuscurida | |
| 4,423,031 A * | 12/1983 | Murui et al. ................. | 424/63 |
| 4,552,755 A | 11/1985 | Randen | |
| 4,720,303 A | 1/1988 | Soldatos | |
| 4,737,541 A | 4/1988 | Stavenger et al. | |
| 4,794,139 A | 12/1988 | Braden et al. | |
| 4,839,166 A | 6/1989 | Grollier et al. | |
| 4,877,557 A | 10/1989 | Kaneshige et al. | |
| 4,927,627 A | 5/1990 | Schrader et al. | |
| 4,939,179 A | 7/1990 | Cheney et al. | |
| 4,971,722 A | 11/1990 | Phillippsen | |
| 4,976,961 A | 12/1990 | Norbury et al. | |
| 5,021,525 A | 6/1991 | Montague et al. | |
| 5,061,481 A | 10/1991 | Suzuki et al. | |
| 5,086,142 A | 2/1992 | Fock et al. | |
| 5,112,601 A | 5/1992 | Sebag et al. | |
| 5,217,636 A | 6/1993 | Paboucek | |
| 5,247,121 A | 9/1993 | Sebag et al. | |
| 5,256,737 A | 10/1993 | Barzaghi | |
| 5,270,379 A | 12/1993 | McAndrew et al. | |
| 5,281,329 A | 1/1994 | Mueller et al. | |
| 5,318,995 A | 6/1994 | Mondet et al. | |
| 5,319,055 A | 6/1994 | Sperry et al. | |
| 5,415,790 A | 5/1995 | Maeda et al. | |
| 5,422,233 A | 6/1995 | Eckert et al. | |
| 5,442,054 A | 8/1995 | Kiesewetter et al. | |
| 5,445,823 A * | 8/1995 | Hall et al. ................... | 424/401 |
| 5,489,427 A * | 2/1996 | Bilbrey ...................... | 424/76.6 |
| 5,516,544 A | 5/1996 | Sekula et al. | |
| 5,519,063 A | 5/1996 | Mondet et al. | |
| 5,525,128 A | 6/1996 | McAleer et al. | |
| 5,530,045 A | 6/1996 | Brena et al. | |
| 5,603,923 A * | 2/1997 | Robinson et al. ............. | 424/60 |
| 5,610,002 A | 3/1997 | Ross et al. | |
| 5,720,961 A * | 2/1998 | Fowler et al. ................ | 424/401 |
| 5,736,125 A | 4/1998 | Morawsky et al. | |
| 5,753,216 A | 5/1998 | Leitch et al. | |
| 5,811,129 A * | 9/1998 | Friedman et al. ............ | 424/535 |
| 5,849,273 A * | 12/1998 | Bonda et al. .................. | 424/59 |
| 5,885,948 A | 3/1999 | Glenn et al. | |
| 5,945,095 A | 8/1999 | Mougin et al. | |
| 5,989,536 A * | 11/1999 | Deckner et al. .......... | 424/78.05 |
| 6,080,707 A | 6/2000 | Glenn et al. | |
| 6,180,123 B1 | 1/2001 | Mondet | |
| 6,180,576 B1 | 1/2001 | Melby et al. | |
| 6,210,656 B1 | 4/2001 | Touzan et al. | |
| 6,238,447 B1 | 5/2001 | More | |
| 6,361,781 B2 | 3/2002 | Lorant | |
| 6,464,969 B2 | 10/2002 | De la Poterie | |

(Continued)

FOREIGN PATENT DOCUMENTS

EP  0803513  10/1997

(Continued)

Primary Examiner—Peter Szekely
(74) *Attorney, Agent, or Firm*—Jeffrey G. Sheldon; Sheldon Mak Rose & Anderson PC

(57) ABSTRACT

Thickeners for oil-containing compositions, particularly cosmetic and personal care compositions, are side chain crystalline polymers which are uniformly dispersed as a crystallized solid in the oil.

60 Claims, No Drawings

U.S. PATENT DOCUMENTS

| | | |
|---|---|---|
| 6,475,495 B1 | 11/2002 | Maignan et al. |
| 6,569,409 B1 | 5/2003 | Hansenne et al. |
| 2002/0031484 A1 | 3/2002 | Douin et al. |
| 2003/0186824 A1 | 10/2003 | Chiu et al. |
| 2005/0272615 A1* | 12/2005 | Bitler .................. 508/325 |

FOREIGN PATENT DOCUMENTS

| | | |
|---|---|---|
| FR | 2131111 | 11/1972 |
| JP | A-59-185813 | 10/1984 |
| JP | 100534 | 4/1992 |
| JP | 07-220531 | 8/1995 |
| WO | WO 96/27641 | 9/1996 |
| WO | WO 98/25710 | 6/1998 |

* cited by examiner

POLYMERIC THICKENERS FOR OIL-CONTAINING COMPOSITIONS

CROSS-REFERENCE TO RELATED APPLICATIONS

This application is a divisional of commonly assigned Ser. No. 09/810,920, filed Mar. 16, 2001 by Steven P. Bitler and David D. Taft, now U.S. Pat. No. 6,989,417. Ser. No. 09/810,920 is a continuation-in-part of, commonly assigned application Ser. No. 09/398,377, filed Sep. 17, 1999, by Steven P. Bitler, now U.S. Pat. No. 7,101,928. The entire disclosure of each of those applications is incorporated herein by reference for all purposes. This application also claims priority from International Application No. PCT/US 00/40780, filed Aug. 30, 2000.

BACKGROUND OF THE INVENTION

1. Field of the Invention

This invention relates to polymeric thickeners for oil-containing compositions.

2. Introduction to the Invention

U.S. Pat. Nos. 4,057,622, 4,057,623, 4,057,624, 5,318,995, 5,519,063 and 5,736,125 disclose the possibility of thickening oil-containing compositions with certain polymers containing (a) lipophilic groups (e.g. in units derived from long chain n-alkyl acrylates) and (b) certain other groups, namely amido groups (in units derived from acrylamide), pyrrolidino groups (in units derived from N-vinyl pyrrolidone), imidazole groups (in units derived from N-vinyl imidazole), carboxylic acid and carboxylic acid salt groups (e.g. in units derived from acrylic or methacrylic acid), sulfonic acid groups, and sulfonic acid salt groups. The disclosure of each of those US patents is incorporated herein by reference. Japanese Kokai No. 4-10054 discloses non-aqueous compositions containing (A) a fluoropolymer containing a perfluoroalkyl group and an alkyl group, either or both of which may be a long chain group, (B) a liquid perfluoroalkyl organic compound, and (C) an oil.

SUMMARY OF THE INVENTION

We have discovered, in accordance with present invention, that a broad range of side chain crystalline (SCC) polymers can be used to thicken oils, provided that the SCC polymer will dissolve in the oil at a temperature above the crystalline melting point of the polymer (referred to herein as $T_p$) and will crystallize when the solution of the polymer in the oil is cooled to a temperature which is below $T_p$ and at which the thickened oil composition is to be used. We believe, though the invention is not dependent upon the correctness of our belief, that the SCC polymer crystallizes into a network in which the polymer crystallites are connected to one another by semi-soluble chains.

The SCC polymers used in the present invention contain lipophilic groups, for example long chain alkyl or substituted alkyl groups, and can, but do not necessarily, contain one or more other groups. They are, however, substantially free of fluorine atoms, carboxylic acid groups, carboxylic acid salt groups, sulfonic acid groups, sulfonic acid salt groups, amido groups, pyrrolidino groups and imidazole groups. The term "substantially free" of these groups is used herein to mean that each of the following conditions is fulfilled by the SCC polymer:

(1) at most 2%, preferably at most 1%, particularly none, of the carbon atoms are substituted by one or more fluorine atoms;

(2) at most 0.5 mol %, preferably at most 0.2 mol %, particularly none, of the repeating units contain a carboxyl group, a carboxyl salt group, a sulfonic acid group, or a sulfonic acid salt group;

(3) at most 1%, preferably at most 0.5%, particularly none, by weight of the repeating units contain a carboxyl group, a carboxyl salt group, a sulfonic acid group, or a sulfonic acid salt group;

(4) the polymer has an acidity of less than 0.1, preferably less than 0.07, meq/g;

(5) at most 2 mol %, preferably at most 1 mol %, particularly none, of the repeating units are derived from acrylamide;

(6) at most 0.5 mol %, preferably at most 0.2 mol %, particularly none, of the repeating units are derived from N-vinylpyrrolidone;

(7) at most 0.5 mol %, preferably at most 0.2 mol %, particularly none, of the repeating units are derived from N-vinylimidazole.

If the SCC polymer contains a substantial number of fluorine atoms, it is more difficult to dissolve in the oil, and this often makes it necessary to add a surfactant in order to achieve solution.

In a first aspect, this invention provides a method of treating a substrate selected from group consisting of human skin, human hair and human nails, the method comprising applying to the substrate a thickened oil composition which is at a temperature $T_s$ and which comprises (1) an oil, and (2) uniformly dispersed in the oil as a crystallized solid, a side chain crystalline (SCC) polymer which (a) has a crystalline melting point, $T_p$, which is greater than $T_s$, and (b) is substantially free of fluorine atoms, carboxylic acid groups, carboxylic acid salt groups, sulfonic acid groups, sulfonic acid salt groups, amido groups, pyrrolidino groups and imidazole groups.

The composition should be maintained at a temperature below $T_p$, since the polymer will have a much reduced thickening effect if it redissolves in the oil. The composition can be free of water, or can contain water. For example it can be a water-in-oil emulsion.

In a second aspect, this invention provides a method of treating a substrate selected from group consisting of human skin, human hair and human nails, the method comprising applying to the substrate a thickened oil composition which comprises (1) an oil, and (2) dispersed in the oil, a polymer which (a) has a crystalline melting point, $T_p$, and an onset of melting temperature, $T_o$, such that $T_p - T_o$ is less than $T_p^{0.7}$;

(b) is soluble in the oil at temperatures above $T_p$, (c) has been dispersed in the oil by a process which comprises (i) dissolving the polymer in the oil at a temperature above $T_p$, and (ii) cooling the solution to crystallize the polymer in the oil, and (d) is a side chain crystalline (SCC) polymer which is substantially free of fluorine atoms, carboxylic acid groups, carboxylic acid salt groups, sulfonic acid groups, sulfonic acid salt groups, amido groups, pyrrolidino groups and imidazole groups;

the composition being at a temperature $T_s$ which is below $T_p$.

An advantage of using these SCC polymers as thickening agents, particularly in water-in-oil emulsions, is that the need to use a surface active agent is reduced or removed. Thus the compositions preferably contain less than 5%, more preferably less than 2%, particularly less than 1%, especially substantially 0%, of surface active agents, the percentages being by weight based on the weight of the oil. This is particularly useful in cosmetic and personal care products, since it is conventional for such products to contain surface active agents (for example the perfluoroalkyl organic compounds used in the compositions disclosed in Japanese Kokai No. 4-100534), and surface active agents can cause an adverse reaction when they contact human skin.

DETAILED DESCRIPTION OF THE INVENTION

In the Summary of the Invention above, and in the Detailed Description of the Invention, the Examples, and the claims below, reference is made to particular features of the invention. It is to be understood that the disclosure of the invention in this specification includes all appropriate combinations of such particular features. For example, where a particular feature is disclosed in the context of a particular embodiment or a particular claim, that feature can also be used, to the extent appropriate, in the context of other particular embodiments and claims, and in the invention generally.

Definitions and Abbreviations

In this specification, parts and percentages are by weight, except where otherwise noted. Temperatures are in ° C. The onset-of-melting temperature, $T_o$, the peak melting temperature, $T_p$, and the heat of fusion, J/g, are determined using a differential scanning calorimeter (DSC) at a rate of temperature change of 10° C./min, for example from −10 to 150° C., and on the second heat cycle. $T_p$ is the temperature at the peak of the DSC curve, and $T_o$ is the temperature at the intersection of the baseline of the DSC peak and the onset line, the onset line being defined as the tangent to the steepest part of the DSC curve below $T_p$. The abbreviations Mn and Mw are used to denote number average and weight average molecular weight in daltons, respectively, measured in tetrahydrofuran using size exclusion chromatography, configured with a Wyatt laser light scattering detector. Bulk viscosities given in the Examples for the polymeric thickeners are in centipoise and were measured using a Brookfield LVT viscometer with an electrically thermostatted Thermosel heater, controlled for example to 95° C., and small sample adapter using spindles 4 and 7.

The abbreviation CxA is used to denote an n-alkyl acrylate in which the n-alkyl group contains x carbon atoms, the abbreviation Cx alkyl is used to denote an n-alkyl group which contains x carbon atoms, and the abbreviation CxM is used to denote an n-alkyl methacrylate in which the n-alkyl group contains x carbon atoms. Other abbreviations are given elsewhere in the specification.

The procedures used in the Examples to compare the effectiveness of the polymeric thickeners were as follows. In Examples 1-8, the thickener, 5 parts, was dissolved in hydrogenated polyisobutylene (HPIB, a light oil), 95 parts, with stirring at 120° C. The resulting solution was placed in an incubator at 20° C. for 16 hours. The viscosity of the cooled product in centipoise was determined using a Brookfield DV-I+digital viscometer with CP-51 spindle using a sample adapter which was thermostatically controlled, for example, to 25° C. The viscosities were measured after four minutes at a speed of 2.5 rpm, i.e. after 10 revolutions. In Examples 9-17, the oil (as identified in Table 2), 14 parts, was heated to 80° C., and the thickener, 0.75 part, was dissolved therein. Water, 35 parts, containing $MgSO_4 \cdot H_2O$, 0.25 part, was heated to 80° C. The oil and the water, both at 80° C., were mixed together, and then cooled to 25° C. with continued stirring. The product, a milky white water-in-oil emulsion, was left overnight, and its viscosity at 25° C. was then measured using a Brookfield cone and plate viscometer. The viscosity was measured after 0.5, 1, 2 and 4 minutes, to assess the effect of shear on the emulsion.

The Polymeric Thickeners

The SCC polymers used as thickeners in the present invention can be homopolymers, or copolymers of two or more comonomers, including random copolymers, graft copolymers and block copolymers (including thermoplastic elastomers). Two or more SCC polymers can be used together. The number average molecular weight of the SCC polymer is generally from 10,000 to 1,500,000, preferably 12,000 to 1,000,000. The molecular weight of an SCC polymer is relatively unimportant to its $T_p$, but is generally an important factor in determining the $T_p$ of other polymers.

The SCC polymer preferably melts over a relatively small temperature range. The closer $T_p$ is to room temperature, the more rapid the transition should preferably be. The SCC polymer preferably has an onset of melting temperature, $T_o$, such that $T_p - T_o$ is less than $T_p^{0.7}$, generally less than $T_p^{0.6}$, particularly less than 10° C., especially less than 6° C., $T_o$ and $T_p$ being in ° C. The crystallinity of the SCC polymer is preferably such that its heat of fusion is at least 20 J/g, particularly at least 40 J/g.

The SCC polymers used in the present invention are in themselves well known. Publications describing SCC polymers include U.S. Pat. Nos. 4,830,855, 5,120,349, 5,156,911, 5,387,450, 5,412,035, 5,665,822, 5,783,302, 5,752,926, 5,807,291, 5,469,867, and 5,826,584; J. Poly. Sci. 60, 19 (1962), J. Poly. Sci, (Polymer Chemistry) 7, 3053 (1969), 9, 1835, 3349, 3351, 3367, 10, 1657, 3347, 18, 2197, 19, 1871, J. Poly. Sci, Poly-Physics Ed 18 2197 (1980), J. Poly. Sci, Macromol. Rev, 8, 117 (1974), Macromolecules 12, 94 (1979), 13, 12, 15, 18, 2141, 19, 611, JACS 75, 3326 (1953), 76; 6280, Polymer J 17, 991 (1985); and Poly. Sci USSR 21, 241 (1979). The entire disclosure of each of these United States Patents is incorporated in this specification by reference.

The SCC polymer may for example be derived from one or more acrylic, methacrylic, olefinic, epoxy, vinyl, ester-containing, amide-containing or ether-containing monomers. Preferred SCC polymers comprise repeating units in which the side chains comprise linear polymethylene radicals containing 10 to 50, e.g. 16-50, especially 16 to 22, carbon atoms. Polymers containing such units can be prepared by polymerizing a monomer component comprising one or more corresponding linear aliphatic acrylates or methacrylates, or equivalent monomers such as acrylamides or methacrylamides. A number of such monomers are available commercially, either as individual monomers or as mixtures of identified monomers, for example C12A, C14A, C16A, C18A, C22A, a mixture of C18A, C20A and C22A, and a mixture of C26A to C40A. The polymers may also contain units derived from one or more other comonomers, for example straight or branched chain alkyl acrylates or methacrylates in which the alkyl group contains less than 12 carbon atoms, and monomers containing suitable functional groups, for example functional groups containing oxygen-, nitrogen- or silicon-containing groups, provided that the polymer is substantially free of fluorine atoms, carboxylic acid groups, carboxylic acid salt groups, sulfonic acid groups, sulfonic acid salt groups, amido groups groups, pyridino groups, and imidazole groups. Such monomers includes those listed below. In the list below, the term (meth)acrylate means that the compound may be either an acrylate or a methacrylate.

(a) Nitrogen-containing monomers, for example N,N-dialkylamino (in particular, dimethylamino) (meth)acrylates; ammonium salt-containing (meth)acrylates, for example 2-trimethylammonium methylmethacrylate chloride, methacrylamidopropyl trimethylammonium chloride, N,N-(diethyl or dimethyl)aminoethyl(meth) acrylate methosulfate; imides like the ring-closed reaction products of maleic or itaconic anhydride with primary amines; 2-methacryloxy-N-ethylmorpholine; 2-t-butylaminoethyl methacrylate; (meth)acrylonitrile; t-butylaminoethyl (meth)acrylate; acryloylmorpholine; N-(2-hydroxyethyl)acetamide and 1-piperidinoethyl (meth)acrylate.

(b) Oxygen-containing monomers which are substantially free of carboxylic acid groups, carboxylic acid salt groups, sulfonic acid groups, sulfonic acid salt groups, and amido groups, for example hydroxyalkyl (in particular, hydroxyethyl, hydroxypropyl, and hydroxybutyl) (meth)acrylates; tetrahydrofurfuryl (meth)acrylate; glycidyl methacrylate; alkoxyalkyl (meth)acrylate, e.g. methoxyethyl (meth)acrylate; 1-acryloxy-2-hydroxy-3-phenoxypropane; methylol methacrylate; ethoxyethyl (meth)acrylate; 2-(2-ethoxyethoxy)ethylacrylate; acetoacetoxyethyl (meth)acrylate; phenoxyethyl (meth) acrylate and (meth)acrolein.

(c) Silicon-containing, e.g. silyl, monomers, for example trimethylsiloxy ethyl(meth)acrylate, 3-acryloxypropyl trimethoxysilane, and 3-acryloxypropyl tris(trimethylsiloxy)silane.

When the SCC polymer is a graft or block copolymer, it can be prepared by copolymerizing a vinyl type macromonomer with other monomers, or by making an SCC polymer, and then reacting the functionalized polymer with the second block material, for example a urethane block, an epoxy block, a polyether block, e.g. a polyethyleneoxide, polypropyleneoxide or polytetramethyleneoxide block, a polysiloxane block, or a poly(alkyl or alkoxy)silane block.

The SCC polymer should contain sufficient long chain groups that it will dissolve in the oil at a temperature above $T_p$. When the SCC polymer is used to thicken an oil or mixture of oils which is free from water, the polymer generally contains at least 50%, preferably at least 60%, particularly at least 70%, especially at least 80%, of units comprising a linear radical containing 10 to 50 carbon atoms, and can contain up to 100% of such units. Particularly when the SCC polymer is used to thicken a water-in-oil emulsion, it may contain at least 5%, preferably at least 10%, of units derived from a monomer containing a hydrophilic group, preferably a hydroxyl group, and may contain higher amounts, e.g. up to 25% or 30%, provided that the SCC polymer will dissolve in the oil.

In one preferred embodiment, the SCC polymer consists essentially of (i) 70-99% by weight of repeating units derived from at least one n-alkyl acrylate or methacrylate ester in which the n-alkyl group contains 16 to 22 carbon atoms, (ii) 1-30%, preferably 15-25%, by weight of repeating units derived from at least one acrylate or methacrylate ester in which the ester group contains a hydroxyl-substituted alkyl group containing less than 12 carbon atoms, and (iii) 0-30% by weight of repeating units derived from at least one acrylate or methacrylate ester in which the ester group contains an unsubstituted alkyl group containing less than 16 carbon atoms.

Suitable polymers within this class include SCC polymers consisting essentially of (i) 70-99% by weight of the repeating units derived from at least one n-alkyl acrylate or methacrylate ester in which the n-alkyl group contains 16 to 22 carbon atoms, and (ii) 1-30%, preferably 15-25%, by weight of the repeating units derived from at least one acrylate or methacrylate ester in which the ester group contains a hydroxyethyl, hydroxypropyl, or hydroxybutyl group.

The molecular weight (and other properties) of the SCC polymer should be sufficiently high that the polymer, after it has been dissolved in the oil, will crystallize in the oil when the heated mixture is cooled to the expected temperature of use, for example to a temperature 10-20° C. below $T_p$, thus producing an opaque mixture.

The $T_p$ of the thickening polymer is preferably 10-40° C. above, particularly 10-30° C. above, especially about 20° C. above, the temperature at which the composition is to be used, which is generally 15-25° C. It appears that the oil plasticizes the thickening polymer, so that its melting point in the composition is for example 5-10° C. lower than $T_p$. It is therefore important that $T_p$ is sufficiently above the temperature of use to ensure that the thickening polymer does not melt during use. Thus for compositions to be used at 20-25° C. the thickening polymer preferably has a $T_p$ of above 40° C., preferably 40-50° C. On the other hand, if the $T_p$ of the thickening polymer is too far above the temperature of use, this can result in excessive crystallization and then precipitation of the polymer, thus reducing the thickening effect. It is preferred, therefore, that $T_p$ is not more than 30° C. above, preferably not more than 20° C. above, the temperature of use. Depending on the expected temperature of use, Tp may be from 0-150° C. generally 10-100° C., for example 40-80° C., preferably 40-50° C., particularly 43-48° C.

The amount of the polymeric thickener preferably used varies with the application. The polymeric thickener should be used in an amount sufficient to thicken the composition to the desired thickness, in general 0.1 to 12% by weight based on the oil, for example 2-10% by weight based on the composition. It is usually unnecessary for the amount of the thickener to be more than 10% by weight based on the weight of the oil. Smaller amounts such as 2 to 7% based on the weight of the oil in compositions which are free of water, and 0.5 to 5% based on the weight of composition in water-in-oil emulsions, are often effective.

Oils

The new polymeric thickeners are effective with a broad range of oils. Suitable oils are disclosed, for example, at column 3, line 37 to column 4, line 4, of U.S. Pat. No. 5,736,125, and elsewhere in the documents incorporated by reference herein. Thus the oil can, for example, comprise at least one oil selected from the group consisting of mineral oils (including for example paraffin oils, vaseline oils, and hydrogenated polyisobutylene); triglycerides (including for example vegetable oils such as sunflower seed oil, sesame seed oil, rape seed oil; sweet almond oil; calphyllum oil, palm oil, avocado oil, jojoba oil, olive oil, castor oil, and grain germ oils); purcellin oil; isopropyl myristate; butyl myristate; cetyl myristate; isopropyl palmitate; butyl palmitate; ethyl-2-hexyl palmitate; isopropyl stearate; butyl stearate; octyl stearate; hexadecyl stearate; isocetyl stearate; decyl oleate; hexyl laurate; propylene glycol dicaprylate, diisopropyl adipate; animal oils (including, for example, perhydrosqualene); silicone oils (including for example dimethyl polysiloxanes, phenyl dimethicones and alkyldimethicones); oleyl alcohol; linoleyl alcohol; linolenyl alcohol; isostearyl alcohol; octyl dodecanol; esters derived from lanolic acid (including for example isopropyl lanolate and isocetyl lanolate); acetyl glycerides; octanoates of alcohols (including for example glycol and glycerol); decanoates of alcohols (including for example glycol and glycerol); and ricinoleates of alcohols (including for example cetyl ricinoleate). For thickening silicone oils, it is preferred to use an SCC polymer containing units derived from a monomer containing silicon, for example a block copolymer containing SCC blocks and polysiloxane blocks. SCC/polysiloxane polymers of this type are described for example in WO 93/07194 and WO 00/04787.

Water-in-oil Emulsions

Water-in-oil emulsions are preferably prepared by mixing together (1) a hot solution of the thickener in the oil and (2) the aqueous phase, the aqueous phase being at a temperature similar to the oil solution (e.g. not more than 10° C. different); and then cooling the mixture while stirring. The ratio of the aqueous phase to the oil phase can be for example 0.5:1 to 9:1.

Compositions

The invention is particularly useful for cosmetic (including hair care) compositions. Such compositions can for example be in the form of varnishes, gels, sticks, oil-in-water creams, water-in-oil creams, and thickened oil products with or without water. Specific examples of such compositions include, but are not limited to lipsticks, deodorant sticks, nail varnishes, pretanning lotions, sunscreen lotions, sun tan lotions, after-sun lotions, sun creams, protective hand creams, night renewal creams, body milks and lotions, light facial creams, protective day creams, liquid moisturizing emulsions, hairdressing preparations (including hair-treating oils, shampoos, after-shampoo compositions, products for rinsing to be applied before or after shampooing, before or after dyeing or bleaching, before or after permanent-waving or hair straightening, as a hair-setting or blow-drying composition, as a restructuring composition, or as a support for permanent-waving or for dyeing or bleaching hair), foam baths, bath oils, skin cleansers, skin foundations mascaras, eye makeups, and makeup removers designed to assist in removing other cosmetic compositions. The cosmetic compositions can contain conventional additives for cosmetic compositions, including but not limited to fragrances, sun screen agents, colorants, pigments, silicones, deodorants and antiseptic agents. The invention is also useful in other contexts, for example in paints, film-forming compositions, inks, and compositions carrying active ingredients such as UV absorbers, fragrances, biocides, antimicrobial agents, germicides, antioxidants, preservatives, disinfectants, enzymes, nutrients, minerals, and drugs (including pharmaceuticals which are active physiologically or pharmacologically, either topically or systemically). Compositions containing a thickener containing an ammonium salt are likely to be useful in certain types of hair care compositions.

The invention is illustrated by the following Examples.

EXAMPLES

Polymers and copolymers were made using the ingredients and amounts thereof shown in the Table below, using the following generalized method. To a resin kettle equipped with overhead stirrer and condenser was added 20% of the monomers and chain transfer agents. The mixture in the resin kettle was heated to 110° C., and oxygen was removed from the system through nitrogen purge for about 30 min followed by addition of 20% of the starting initiator charge. After allowing sufficient time for any initial exotherm to abate, the remaining monomers, chain transfer agents and starting initiator were pumped into the reaction vessel over 60-90 min. The polymer mixture was allowed to continue reacting for 60 min followed by addition of the chase initiator and reaction for 60 min. The mixture was put under reduced pressure for 60 min to removal volatile residuals. The resulting polymers were generally yellow to white solids. The molecular weight, $T_p$, and viscosity of each sample were measured. The effectiveness of the polymers as thickeners was measured as described above, and the results are shown in Tables 1 and 2 below.

The following abbreviations are used in the Tables. ME=mercaptoethanol; MA=methacrylic acid; DMAEA=N,N-dimethylaminoethyl acrylate; HEA=2-hydroxyethyl acrylate; TAPO=t-amylperoxy 2-ethylhexanoate sold by Witco as Esperox 570P, 75% active in liquid; TBPB=t-butylperoxybenzoate sold by Witco as Esperox 10; Estol is propylene glycol dicaprylate/caprate sold by Uniqema under the tradename Estol 1526; Min'l is mineral oil; and opq=opaque in appearance.

TABLE 1

|  | Example | | | | | |
| --- | --- | --- | --- | --- | --- | --- |
|  | 1 | 2 | 3 | 4 | 5 | 6 |
| C16A |  |  |  | 95 |  |  |
| C18A | 80 |  | 95 |  | 100 | 85 |
| C22A |  | 95 |  |  |  |  |
| HEA | 20 |  |  |  |  |  |
| DMAEA |  |  |  |  |  | 15 |
| MA |  | 5 | 5 | 5 |  |  |
| ME | 0.34 | 0.17 | 0.17 | 0.17 | 0.17 | 0.1 |
| TAPO | 1.73 | 1.73 | 1.73 | 1.73 | 1.73 | 1.73 |
| TAPB | 0.67 | 0.67 |  |  |  |  |
| TBPB |  |  | 0.5 | 0.5 | 0.5 | 0.5 |
| Tp° C. | 48 | 67 | 47 | 39 | 50 | 45 |
| J/g | 56 | 99 | 57 | 64 | 73 | 60 |
| Mw | 236K |  | 427K | 1,000K | 950K |  |
| Mn | 52K |  | 240K | 520K | 230K |  |
| Bulk viscosity | 4,000 | 2,500 | 19,000 | 24,000 | 2,000 | 350 |
| Visc in HPIB | 12,600 | 164 | 2600 | <50 | 5400 | 6000 |
|  | opq | opq | opq | clear | opq | opq |

In Example 2, the polymer had a $T_p$ above the preferred range of 40-50° C., which resulted in excessive crystallinity and poor thickening under the test conditions. In Example 4, the polymer had a $T_p$ below the preferred range, and was ineffective as a thickener under the test conditions, because it did not crystallize on cooling.

TABLE 2

|  | Example | | | | | |
| --- | --- | --- | --- | --- | --- | --- |
|  | 7 | 8 | 9 | 10 | 11 | 12 |
| C18A | 80 | 80 | 80 | 100 | 100 | 100 |
| HEA | 20 | 20 | 20 | | | |
| ME | 0.34 | 0.34 | 0.34 | 0.17 | 0.17 | 0.17 |
| TAPO | 1.73 | 1.73 | 1.73 | 1.73 | 1.73 | 1.73 |
| TAPB | 0.67 | 0.67 | 0.67 | | | |
| TBPB | | | | 0.5 | 0.5 | 0.5 |
| Tp° C. | 48 | 48 | 48 | 50 | 50 | 50 |
| J/g | 56 | 56 | 56 | 73 | 73 | 73 |
| Mw | 236K | 236K. | 236K | 950K. | 950K. | 950K. |
| Mn | 52K | 52K. | 52K. | 230K. | 230K. | 230K. |
| Bulk viscosity | 4,000 | 4,000 | 4,000 | 2,000 | 2,000 | 2,000 |
| Oil | HPIB | Min'l | Estol | HPIB | Min'l | Estol |
| Viscosity after | | | | | | |
| 0.5 min | 35K | 37K | 45K | 29K | ** | ** |
| 1.0 min | 35K | 38K | 40K | 28K | | |
| 2.0 min | 41K | 38K | 34K | 25K | | |
| 4.0 min | 46K | 40K | 34K | 28K | | |

** separated.

The invention has been described by reference to the use of SCC polymers. However, other polymers with the same crystallinity characteristics give similar results, and their use as thickeners for oils forms part of the present invention. Such other polymers include for example polymers in which the crystallinity results exclusively or predominantly from the polymer backbone, e.g. polymers of α-olefins containing 2 to 12, preferably 2 to 8, carbon atoms, e.g. polymers of monomers having the formula $CH_2=CHR$, where R is hydrogen, methyl, propyl, butyl, pentyl, 4-methylpentyl, hexyl or heptyl, as well as other polymers such as polyesters, polyamides, for example homopolymers and copolymers of caprolactone, and polyalkylene oxides, for example polytetrahydrofuran.

What is claimed is:

1. A method of treating a substrate selected from human skin, human hair and human nails, the method comprising applying to the substrate a thickened oil composition which is free of water and which comprises
   (1) an oil, and
   (2) dispersed in the oil, a side chain crystalline (SCC) polymer which
      (a) has a crystalline melting point $T_p$, and an onset of melting temperature, $T_o$, such that $(T_p-T_o)$ is less than $T_p^{0.7}$;
      (b) is soluble in the oil at temperatures above $T_p$,
      (c) has been dispersed in the oil by a process which comprises
         (i) dissolving the polymer in the oil at the temperature above $T_p$, and
         (ii) cooling the solution to crystallize the polymer in the oil, and
      (d) is substantially free of fluorine atoms, carboxylic acid groups, carboxylic acid salt groups, sulfonic acid groups, sulfonic acid salt groups, amido groups, pyrrolidino groups and imidazole groups; and
   the composition being at a temperature $T_s$ which is below $T_p$, wherein the SCC polymer consists essentially of
      (i) 70-99% by weight of repeating units derived from at least one n-alkyl acrylate or methacrylate ester in which the n-alkyl group contains 16 to 22 carbon atoms,
      (ii) 1-30% by weight of repeating units derived from at least one acrylate or methacrylate ester in which the ester group contains a hydroxyl-substituted alkyl group containing less than 12 carbon atoms, and
      (iii) 0-29% by weight of repeating units derived from at least one acrylate or methacrylate ester in which the ester group contains an unsubstituted alkyl group containing less than 16 carbon atoms.

2. A method according to claim 1 wherein the composition is at a temperature $T_s$, where $T_s$ is from 15 to 25° C., and wherein the SCC polymer has a crystalline melting point, $T_p$, which is 10 to 30° C. above $T_s$.

3. A method according to claim 1 wherein the SCC polymer has a heat of fusion of at least 20 J/g, and an onset-of melting-point $T_o$ such that $(T_p-T_o)$ is less than 10° C.

4. A method according to claim 1 wherein the hydroxyl-substituted alkyl group is a hydroxyethyl, hydroxypropyl, or hydroxybutyl group.

5. A method according to claim 1 wherein the composition contains less than 1% by weight of surface active agents, based on weight of the oil.

6. A method according to claim 1 wherein each of the following conditions is fulfilled by the SCC polymer:
   (1) at most 1% of the carbon atoms are substituted by one or more fluorine atoms;
   (2) at most 0.2 mol % of the repeating units contain a carboxyl group, a carboxyl salt group, a sulfonic acid group, or a sulfonic acid salt group;

(3) at most 0.5% by weight of the repeating units contain a carboxyl group, a carboxyl salt group, a sulfonic acid group, or a sulfonic acid salt group;
(4) the polymer has an acidity of less than 0.07 meq/g;
(5) at most 1 mol % of the repeating units are derived from acrylamide
(6) at most 0.2 mol % of the repeating units are derived from N-vinylpyrrolidone;
(7) at most 0.2 mol % of the repeating units are derived from N-vinylimidazole.

7. A method according to claim 1 wherein each of the following conditions is fulfilled by the SCC polymer:
(1) none of the carbon atoms are substituted by one or more fluorine atoms;
(2) none of the repeating units contain a carboxyl group, a carboxyl salt group, a sulfonic acid group, or a sulfonic acid salt group;
(3) none of the repeating units contain a carboxyl group, a carboxyl salt group, a sulfonic acid group, or a sulfonic acid salt group;
(4) the polymer has an acidity of less than 0.07 meq/g;
(5) none of the repeating units are derived from acrylamide;
(6) none of the repeating units are derived from N-vinylpyrrolidone;
(7) none of the repeating units are derived from N-vinylimidazole.

8. A method of treating a substrate selected from human skin, human hair and human nails, the method comprising applying to the substrate a thickened oil composition which comprises
(1) a silicone oil, and
(2) uniformly dispersed in the oil as a crystallized solid, a side chain crystalline (SCC) polymer which contains units derived from a monomer containing silicon and which is substantially free of fluorine atoms, carboxylic acid groups, carboxylic acid salt groups, sulfonic acid groups, sulfonic acid salt groups, amido groups, pyrrolidino groups and imidazole groups.

9. A method according to claim 8 wherein the SCC polymer is a block copolymer containing SCC blocks and polysiloxane blocks.

10. A method according to claim 8 wherein the SCC polymer has a crystalline melting point, $T_p$, of 40-80° C.

11. A method according to claim 8 wherein the SCC polymer has a heat of fusion of at least 20 J/g and an onset-of-melting point, $T_o$, such that $(T_p-T_o)$ is less than 10° C.

12. A method according to claim 8 wherein each of the following conditions is fulfilled by the SCC polymer:
(1) at most 1% of the carbon atoms are substituted by one or more fluorine atoms;
(2) at most 0.2 mol % of the repeating units contain a carboxyl group, a carboxyl salt group, a sulfonic acid group, or a sulfonic acid salt group;
(3) at most 0.5% by weight of the repeating units contain a carboxyl group, a carboxyl salt group, a sulfonic acid group, or a sulfonic acid salt group;
(4) the polymer has an acidity of less than 0.07 meq/g;
(5) at most 1 mol % of the repeating units are derived from acrylamide
(6) at most 0.2 mol % of the repeating units are derived from N-vinylpyrrolidone;
(7) at most 0.2 mol % of the repeating units are derived from N-vinylimidazole.

13. A method according to claim 8 wherein each of the following conditions is fulfilled by the SCC polymer:
(1) none of the carbon atoms are substituted by one or more fluorine atoms;
(2) none of the repeating units contain a carboxyl group, a carboxyl salt group, a sulfonic acid group, or a sulfonic acid salt group;
(3) none of the repeating units contain a carboxyl group, a carboxyl salt group, a sulfonic acid group, or a sulfonic acid salt group;
(4) the polymer has an acidity of less than 0.07 meq/g;
(5) none of the repeating units are derived from acrylamide;
(6) none of the repeating units are derived from N-vinylpyrrolidone;
(7) none of the repeating units are derived from N-vinylimidazole.

14. A cosmetic composition comprising
(a) a mixture of two or more polymers,
at least one of the polymers being a side chain crystalline (SCC) polymer which
(i) has a melting point from 40° C. to 80° C.,
(ii) consists of repeating units which are derived from at least one n-alkyl acrylate or methacrylate in which the n-alkyl group contains 18 to 50 carbon atoms,
(iii) is substantially free of fluorine atoms, carboxylic acid groups, carboxylic acid salt groups, sulfonic acid groups, sulfonic acid salt groups, amido groups, pyrrolidino groups and imidazole groups, and
(iii) is capable of forming a hydrophobic film at room temperature, and
(b) at least one oil;
the mixture of polymers being uniformly dispersed in the oil as a crystallized solid.

15. A cosmetic composition according to claim 14 which comprises a mixture of two or more side chain crystalline (SCC) polymers.

16. A process for thickening a cosmetic composition comprising an oil phase, the process comprising dispersing in the oil phase a mixture of two or more side chain crystalline (SCC) polymers,
at least one of the SCC polymers being solid at ambient temperature and having a melting temperature of 40 to 50° C.;
at least one of the SCC polymers being solid at ambient temperature and having a melting temperature at least equal to 50° C.;
at least one of the SCC polymers consisting of repeating units which are derived from an n-alkyl acrylate or methacrylate in which the n-alkyl group contains 18 to 50 carbon atoms; and
at least one of the SCC polymers being substantially free of fluorine atoms, carboxylic acid groups, carboxylic acid salt groups, sulfonic acid groups, sulfonic acid salt groups, amido groups, pyrrolidino groups and imidazole groups.

17. A process for thickening a cosmetic composition comprising an oil phase, the process comprising dispersing in the oil phase a mixture of (a) an SCC polymer comprising units derived from stearyl acrylate, and (b) an SCC polymer comprising units derived from behenyl acrylate, at least one of the SCC polymers being substantially free of fluorine atoms, carboxylic acid groups, carboxylic acid salt groups, sulfonic acid groups, sulfonic acid salt groups, amido groups, pyrrolidino groups and imidazole groups.

18. A process according to claim 17 wherein the SCC polymer derived from stearyl acrylate is a homopolymer of stearyl acrylate, and the SCC polymer derived from behenyl acrylate is a homopolymer of behenyl acrylate.

19. A lipstick comprising:
   at least one oil phase structured by a mixture of two or more side chain crystalline (SCC) polymers,
      at least one of the SCC polymers being solid at ambient temperature and having a melting temperature of 40 to 50° C.;
      at least one of the SCC polymers being solid at ambient temperature and having a melting temperature at least equal to 50° C.; and
      at least one of the SCC polymers being substantially free of fluorine atoms, carboxylic acid groups, carboxylic acid salt groups, sulfonic acid groups, sulfonic acid salt groups, amido groups, pyrrolidino groups and imidazole groups.

20. A lipstick comprising:
   at least one oil phase structured by a mixture of (a) a homopolymer of stearyl acrylate, and (b) a homopolymer of behenyl acrylate.

21. A method of treating a substrate selected from human skin, human hair and human nails, the method comprising applying to the substrate a thickened oil composition which is free of water and which comprises
   (1) an oil, and
   (2) uniformly dispersed in the oil as a crystallized solid, a side chain crystalline (SCC) polymer which
      (a) has a crystalline melting point, $T_p$, and an onset of melting temperature, $T_o$, such that $(T_p-T_o)$ is less than $T_p^{0.7}$, and
      (b) is substantially free of fluorine atoms, carboxylic acid groups, carboxylic acid salt groups, sulfonic acid groups, sulfonic acid salt groups, amido groups, pyrrolidino groups and imidazole groups.

22. A method according to claim 21 wherein the SCC polymer consists essentially of
   (i) 20-99% by weight of repeating units derived from at least one n-alkyl acrylate or methacrylate ester in which the n-alkyl group contains 16 to 22 carbon atoms,
   (ii) 1-30% by weight of repeating units derived from at least one acrylate or methacrylate ester in which the ester group contains a hydroxyl-substituted alkyl group containing less than 12 carbon atoms, and
   (iii) 0-29% by weight of repeating units derived from at least one acrylate or methacrylate ester in which the ester group contains an unsubstituted alkyl group containing less than 16 carbon atoms.

23. A method according to claim 21 wherein the hydroxyl-substituted alkyl group is a hydroxyethyl, hydroxypropyl, or hydroxybutyl group.

24. A method according to claim 21 wherein the SCC polymer has an onset of melting temperature, $T_o$, such that $(T_p-T_o)$ is less than $T_p^{0.6}$.

25. A method according to claim 21 wherein the composition is at a temperature $T_s$, where $T_s$ is from 15 to 25° C., and wherein the SCC polymer has a crystalline melting point, $T_p$, which is 10 to 30° C. above $T_s$.

26. A method according to claim 21 wherein the SCC polymer has a heat of fusion of at least 20 J/g, and an onset-of-melting point $T_o$ such that $(T_p-T_o)$ is less then 10° C.

27. A method according to claim 21 wherein $T_p$ is 40 to 80° C.

28. A method according to claim 21 wherein the composition contains less than 1% by weight of surface active agents, based on weight of the oil.

29. A method according to claim 21 wherein each of the following conditions is fulfilled by the SCC polymer:
   (1) at most 1% of the carbon atoms are substituted by one or more fluorine atoms;
   (2) at most 0.2 mol % of the repeating units contain a carboxyl group, a carboxyl salt group, a sulfonic acid group, or a sulfonic acid salt group;
   (3) at most 0.5% by weight of the repeating units contain a carboxyl group, a carboxyl salt group, a sulfonic acid group, or a sulfonic acid salt group;
   (4) the polymer has an acidity of less than 0.07 meq/g;
   (5) at most 1 mol % of the repeating units are derived from acrylamide
   (6) at most 0.2 mol % of the repeating units are derived from N-vinylpyrrolidone;
   (7) at most 0.2 mol % of the repeating units are derived from N-vinylimidazole.

30. A method according to claim 21 wherein each of the following conditions is fulfilled by the SCC polymer:
   (1) none of the carbon atoms are substituted by one or more fluorine atoms;
   (2) none of the repeating units contain a carboxyl group, a carboxyl salt group, a sulfonic acid group, or a sulfonic acid salt group;
   (3) none of the repeating units contain a carboxyl group, a carboxyl salt group, a sulfonic acid group, or a sulfonic acid salt group;
   (4) the polymer has an acidity of less than 0.07 meq/g;
   (5) none of the repeating units are derived from acrylamide;
   (6) none of the repeating units are derived from N-vinylpyrrolidone;
   (7) none of the repeating units are derived from N-vinylimidazole.

31. A method of treating a substrate selected from human skin, human hair and human nails, the method comprising applying to the substrate a thickened oil composition which is free from water and which comprises
   (1) an oil, and
   (2) dispersed in the oil, a side chain crystalline (SCC) polymer which
      (a) has a crystalline melting point $T_p$, and an onset of melting temperature, $T_o$, such that $(T_p-T_o)$ is less than $T_p^{0.7}$;
      (b) is soluble in the oil at temperatures above $T_p$,
      (c) has been dispersed in the oil by a process which comprises
         (i) dissolving the polymer in the oil at the temperature above $T_p$, and
         (ii) cooling the solution to crystallize the polymer in the oil, and
      (d) is substantially free of fluorine atoms, carboxylic acid groups, carboxylic acid salt groups, sulfonic acid groups, sulfonic acid salt groups, amido groups, pyrrolidino groups and imidazole groups; and
   the composition being at a temperature $T_s$ which is below $T_p$.

32. A method according to claim 31 wherein the composition is at a temperature $T_s$, where $T_s$ is from 15 to 25° C., and wherein the SCC polymer has a crystalline melting point, $T_p$, which is 10 to 30° C. above $T_s$.

33. A method according to claim 31 wherein the SCC polymer consists essentially of
   (i) 70-99% by weight of repeating units derived from at least one n-alkyl acrylate or methacrylate ester in which the n-alkyl group contains 16 to 22 carbon atoms,
   (ii) 1-30% by weight of repeating units derived from at least one acrylate or methacrylate ester in which the ester group contains a hydroxyl-substituted alkyl group containing less than 12 carbon atoms, and
(iii) 0-29% by weight of repeating units derived from at least one acrylate or methacrylate ester in which the ester group contains an unsubstituted alkyl group containing less than 16 carbon atoms.

34. A method according to claim 31 wherein the hydroxyl-substituted alkyl group is a hydroxyethyl, hydroxypropyl, or hydroxybutyl group.

35. A method according to claim 31 wherein the SCC polymer has an onset of melting temperature, $T_o$, such that $(T_p-T_o)$ is less than $T_p^{0.6}$.

36. A method according to claim 31 wherein the SCC polymer has a heat of fusion of at least 20 J/g, and an onset-of-melting point $T_o$ such that $(T_p-T_o)$ is less than 10° C.

37. A method according to claim 31 wherein the composition contains less than 1% by weight of surface active agents, based on weight of the oil.

38. A method according to claim 31 wherein each of the following conditions is fulfilled by the SCC polymer.
    (1) at most 1% of the carbon atoms are substituted by one or more fluorine atoms;
    (2) at most 0.2 mol % of the repeating units contain a carboxyl group, a carboxyl salt group, a sulfonic acid group, or a sulfonic acid salt group;
    (3) at most 0.5% by weight of the repeating units contain a carboxyl group, a carboxyl salt group, a sulfonic acid group, or a sulfonic acid salt group;
    (4) the polymer has an acidity of less than 0.07 meq/g;
    (5) at most 1 mol % of the repeating units are derived from acrylamide
    (6) at most 0.2 mol % of the repeating units are derived from N-vinylpyrrolidone;
    (7) at most 0.2 mol % of the repeating units are derived from N-vinylimidazole.

39. A method according to claim 31 wherein each of the following conditions is fulfilled by the SCC polymer:
    (1) none of the carbon atoms are substituted by one or more fluorine atoms;
    (2) none of the repeating units contain a carboxyl group, a carboxyl salt group, a sulfonic acid group, or a sulfonic acid salt group;
    (3) none of the repeating units contain a carboxyl group, a carboxyl salt group, a sulfonic acid group, or a sulfonic acid salt group;
    (4) the polymer has an acidity of less than 0.07 meq/g;
    (5) none of the repeating units are derived from acrylamide;
    (6) none of the repeating units are derived from N-vinylpyrrolidone;
    (7) none of the repeating units are derived from N-vinylimidazole.

40. A method according to claim 21 wherein the side chain crystalline (SCC) polymer
    (a) has a crystalline melting point, $T_p$, and an onset of melting temperature, $T_o$, such that $T_p-T_o$, is less than $T_p^{0.7}$, and
    (b) comprises repeating units in which the side chains comprise linear polymethylene moieties containing 18 to 50 carbon atoms, and
    (c) is substantially free of fluorine atoms, carboxylic acid groups, carboxylic acid salt groups, sulfonic acid groups, sulfonic acid salt groups, amido groups, pyrrolidino groups and imidazole groups.

41. A method of treating a substrate selected from human skin, human hair and human nails, the method comprising applying to the substrate a thickened oil composition which comprises
    (1) an oil, and
    (2) dispersed in the oil, a side chain crystalline (SCC) polymer which
        (a) has a crystalline melting point $T_p$, and an onset of melting temperature, $T_o$, such that $(T_p-T_o)$ is less than $T_p^{0.7}$;
        (b) consists of repeating units in which the side chains comprise linear polymethylene moieties containing 18 to 50 carbon atoms,
        (c) is substantially free of fluorine atoms, carboxylic acid groups, carboxylic acid salt groups, sulfonic acid groups, sulfonic acid salt groups, amido groups, pyrrolidino groups and imidazole groups, and
        (d) has been dispersed in the oil by a process which comprises
            (i) dissolving the polymer in the oil at the temperature above $T_p$, and
            (ii) cooling the solution to crystallize the polymer in the oil;
the composition being at a temperature $T_s$ which is below $T_p$.

42. A method according to claim 41 wherein the composition is a water-in-oil emulsion or an oil-in-water emulsion.

43. A method according to claim 41 wherein the composition is free from water.

44. A method according to claim 41 wherein the composition is at a temperature $T_s$, where $T_s$ is from 15 to 25° C., and wherein the SCC polymer has a crystalline melting point, $T_p$, which is 10 to 30° C. above $T_s$.

45. A method according to claim 41 wherein the SCC polymer has an onset of melting temperature, $T_o$, such that $(T_p-T_o)$ is less than $T_p^{0.6}$.

46. A method according to claim 41 wherein the SCC polymer has an onset of melting temperature, $T_o$, such that $(T_p-T_o)$ is less than 10° C.

47. A method according to claim 41 wherein the SCC polymer has a heat of fusion of at least 20 J/g.

48. A method according to claim 41 wherein the composition contains less than 1% by weight of surface active agents, based on weight of the oil.

49. A method according to claim 41 wherein each of the following conditions is fulfilled by the SCC polymer:
    (1) at most 1% of the carbon atoms are substituted by one or more fluorine atoms;
    (2) at most 0.2 mol % of the repeating units contain a carboxyl group, a carboxyl salt group, a sulfonic acid group, or a sulfonic acid salt group;
    (3) at most 0.5% by weight of the repeating units contain a carboxyl group, a carboxyl salt group, a sulfonic acid group, or a sulfonic acid salt group;
    (4) the polymer has an acidity of less than 0.07 meq/g;
    (5) at most 1 mol % of the repeating units are derived from acrylamide
    (6) at most 0.2 mol % of the repeating units are derived from N-vinylpyrrolidone;
    (7) at most 0.2 mol % of the repeating units are derived from N-vinylimidazole.

50. A method according to claim 41 wherein each of the following conditions is fulfilled by the SCC polymer:
    (1) none of the carbon atoms are substituted by one or more fluorine atoms;
    (2) none of the repeating units contain a carboxyl group, a carboxyl salt group, a sulfonic acid group, or a sulfonic acid salt group;

(3) none of the repeating units contain a carboxyl group, a carboxyl salt group, a sulfonic acid group, or a sulfonic acid salt group;

(4) the polymer has an acidity of less than 0.07 meq/g;

(5) none of the repeating units are derived from acrylamide;

(6) none of the repeating units are derived from N-vinylpyrrolidone;

(7) none of the repeating units are derived from N-vinylimidazole.

51. A method according to claim 21 wherein the composition is a nail varnish, lipstick, deodorant stick, a hairdressing preparation, foam bath, bath oil or mascara.

52. A method of treating a substrate selected from human skin, human hair and human nails, the method comprising applying to the substrate a thickened oil composition which is free of water, which is a nail varnish, lipstick, deodorant stick, a hairdressing preparation, foam bath, bath oil or mascara, and which comprises (1) an oil, and (2) dispersed in the oil, a side chain crystalline (SCC) polymer which (a) has a crystalline melting point $T_p$, and an onset of melting temperature, $T_o$, such that $(T_p-T_o)$ is less than $T_p^{0.7}$;

(b) is soluble in the oil at temperatures above $T_p$, (c) has been dispersed in the oil by a process which comprises (i) dissolving the polymer in the oil at the temperature above $T_p$, and (ii) cooling the solution to crystallize the polymer in the oil, and (d) is substantially free of fluorine atoms, carboxylic acid groups, carboxylic acid salt groups, sulfonic acid groups, sulfonic acid salt groups, amido groups, pyrrolidino groups and imidazole groups; and the composition being at a temperature $T_s$ which is below $T_p$.

53. A method according to claim 52 wherein the composition is at a temperature $T_s$, where $T_s$ is from 15 to 25° C., and wherein the SCC polymer has a crystalline melting point, $T_p$, which is 10 to 30° C. above $T_s$.

54. A method according to claim 52 wherein the SCC polymer has an onset of melting temperature, $T_o$, such that $T_p-T_o$ is less than $T_p^{0.}$.

55. A method according to claim 52 wherein the SCC polymer has a heat of fusion of at least 20 J/g, and an onset-of-melting point $T_o$ such that $(T_p-T_o)$ is less than 10° C.

56. A method of treating a substrate selected from human skin, human hair and human nails, the method comprising applying to the substrate a thickened oil composition which is a nail varnish, lipstick, deodorant stick, a hairdressing preparation, foam bath, bath oil or mascara, and which comprises (1) an oil, and (2) dispersed in the oil, a side chain crystalline (SCC) polymer which (a) has a crystalline melting point $T_p$, and an onset of melting temperature, $T_o$, such that $(T_p-T_o)$ is less than $T_p^{0.7}$;

(b) is soluble in the oil at temperatures above $T_p$, and (c) consists essentially of (i) 70-99% by weight of repeating units derived from at least one n-alkyl acrylate or methacrylate ester in which the n-alkyl group contains 16 to 22 carbon atoms, (ii) 1-30% by weight of repeating units derived from at least one acrylate or methacrylate ester in which the ester group contains a hydroxyl-substituted alkyl group containing less than 12 carbon atoms, and (iii) 0-29% by weight of repeating units derived from at least one acrylate or methacrylate ester in which the ester group contains an unsubstituted alkyl group containing less than 16 carbon atoms;

(d) is substantially free of fluorine atoms, carboxylic acid groups, carboxylic acid salt groups, sulfonic acid groups, sulfonic acid salt groups, amido groups, pyrrolidino groups and imidazole groups; and (e) has been dispersed in the oil by a process which comprises (i) dissolving the polymer in the oil at the temperature above $T_p$, and (ii) cooling the solution to crystallize the polymer in the oil;

the composition being at a temperature $T_s$ which is below $T_p$.

57. A method according to claim 56 wherein the hydroxyl-substituted alkyl group is a hydroxyethyl, hydroxypropyl, or hydroxybutyl group.

58. A method according to claim 52 wherein the composition contains less than 1% by weight of surface active agents, based on weight of the oil.

59. A method according to claim 52 wherein each of the following conditions is fulfilled by the SCC polymer:

(1) at most 1% of the carbon atoms are substituted by one or more fluorine atoms;

(2) at most 0.2 mol % of the repeating units contain a carboxyl group, a carboxyl salt group, a sulfonic acid group, or a sulfonic acid salt group;

(3) at most 0.5% by weight of the repeating units contain a carboxyl group, a carboxyl salt group, a sulfonic acid group, or a sulfonic acid salt group;

(4) the polymer has an acidity of less than 0.07 meq/g;

(5) at most 1 mol % of the repeating units are derived from acrylamide (6) at most 0.2 mol % of the repeating units are derived from N-vinylpyrrolidone;

(7) at most 0.2 mol % of the repeating units are derived from N-vinylimidazole.

60. A method according to claim 52 wherein each of the following conditions is fulfilled by the SCC polymer:

(1) none of the carbon atoms are substituted by one or more fluorine atoms, (2) none of the repeating units contain a carboxyl group, a carboxyl salt group, a sulfonic acid group, or a sulfonic acid salt group;

(3) none of the repeating units contain a carboxyl group, a carboxyl salt group, a sulfonic acid group, or a sulfonic acid salt group;

(4) the polymer has an acidity of less than 0.07 meq/g;

(5) none of the repeating units are derived from acrylamide;

(6) none of the repeating units are derived from N-vinylpyrrolidone;

(7) none of the repeating units are derived from N-vinylimidazole.

* * * * *